(12) United States Patent
Altamirano

(10) Patent No.: US 9,408,628 B2
(45) Date of Patent: *Aug. 9, 2016

(54) SURGICAL INSTRUMENT EQUIPMENT APPROPRIATE FOR MINI-INVASIVE SURGERY

(75) Inventor: José Daniel Altamirano, Concepción (AR)

(73) Assignee: Wom Industrias SRL, Provincia de Tucuman (AR)

( * ) Notice: Subject to any disclaimer, the term of this patent is extended or adjusted under 35 U.S.C. 154(b) by 1049 days.

This patent is subject to a terminal disclaimer.

(21) Appl. No.: 13/132,250

(22) PCT Filed: Jan. 6, 2010

(86) PCT No.: PCT/EC2010/000012
§ 371 (c)(1),
(2), (4) Date: Jun. 1, 2011

(87) PCT Pub. No.: WO2010/081482
PCT Pub. Date: Jul. 22, 2010

(65) Prior Publication Data
US 2011/0230869 A1  Sep. 22, 2011

(30) Foreign Application Priority Data
Jan. 16, 2009  (AR) .................... P090100135

(51) Int. Cl.
| | | |
|---|---|---|
| *A61B 17/00* | (2006.01) |
| *A61B 1/32* | (2006.01) |
| *A61B 17/34* | (2006.01) |
| *A61B 18/14* | (2006.01) |
| A61B 17/02 | (2006.01) |
| A61B 17/29 | (2006.01) |

(52) U.S. Cl.
CPC .......... *A61B 17/3423* (2013.01); *A61B 18/1445* (2013.01); *A61B 90/57* (2016.02); *A61B 17/0218* (2013.01); *A61B 2017/2904* (2013.01); *A61B 2017/2912* (2013.01); *A61B 2017/2931* (2013.01); *A61B 2017/3447* (2013.01)

(58) Field of Classification Search
CPC ............................. A61B 19/22; A61B 19/201
See application file for complete search history.

(56) References Cited

U.S. PATENT DOCUMENTS

| | | | |
|---|---|---|---|
| 5,352,219 A | 10/1994 | Reddy | |
| 5,441,059 A | 8/1995 | Dannan | |
| 6,723,043 B2 | 4/2004 | Kleeman et al. | |
| 6,963,792 B1 * | 11/2005 | Green ................ | A61B 1/00193 348/E13.014 |
| 7,753,901 B2 * | 7/2010 | Piskun et al. .................. | 604/539 |
| 8,257,254 B2 * | 9/2012 | Piskun .......................... | 600/208 |

(Continued)

FOREIGN PATENT DOCUMENTS

ES    2 247 419 T3    3/2006

*Primary Examiner* — William Thomson
*Assistant Examiner* — Jeffrey Lipitz
(74) *Attorney, Agent, or Firm* — Sughrue Mion, PLLC

(57) ABSTRACT

Equipment of surgical instruments suitable for minimally invasive surgery, comprised by a multivalve device with adjustable separator to enter the patient's body and with at least one access simultaneous port for a number of components which includes an operative surgical device comprised by a control, a movement transmission element and an operative mounting clamp of a needle plier comprised by a control, a head connecting sheath, with a connecting needle lodged in its interior and the operative head; and a cauterization device comprised by a control, a movement transmitting element and the cautery.

17 Claims, 6 Drawing Sheets

(56) References Cited

U.S. PATENT DOCUMENTS

| | | |
|---|---|---|
| 2003/0060687 A1 | 3/2003 | Kleeman et al. |
| 2003/0120290 A1* | 6/2003 | Danitz ............... A61B 17/122 606/151 |
| 2008/0255519 A1 | 10/2008 | Pikun et al. |
| 2008/0287926 A1 | 11/2008 | Abou El Kheir |
| 2009/0248041 A1* | 10/2009 | Williams ............. A61B 8/12 606/130 |

* cited by examiner

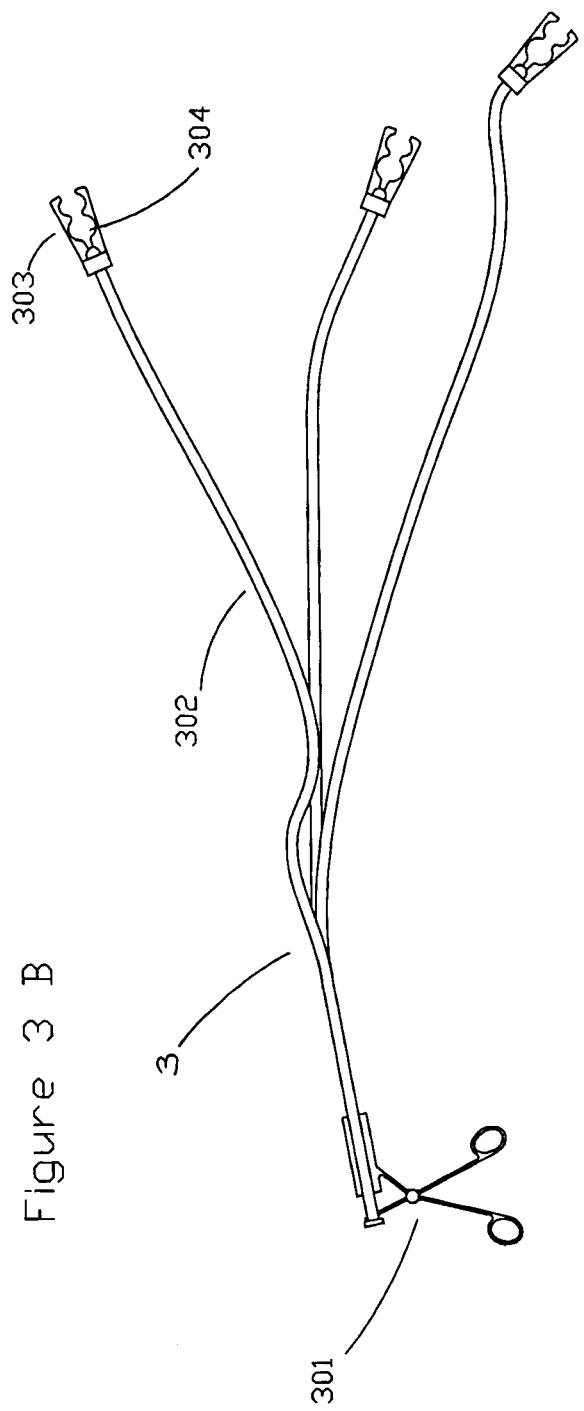

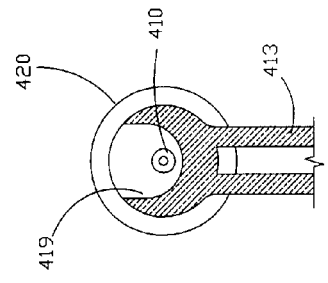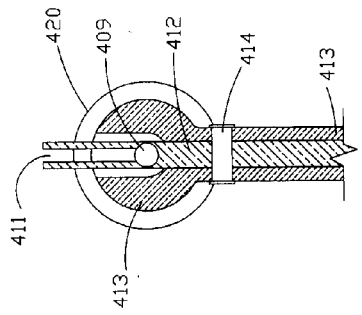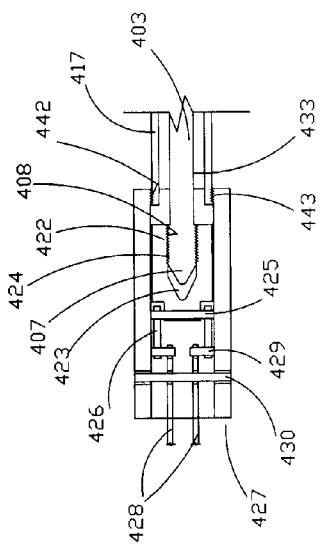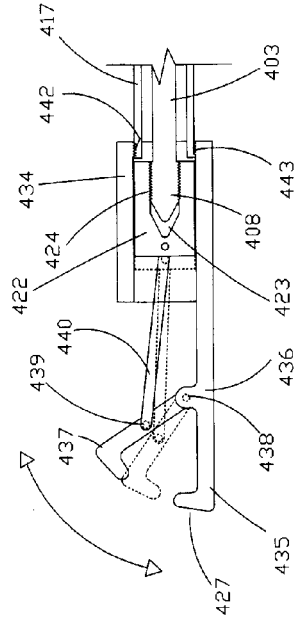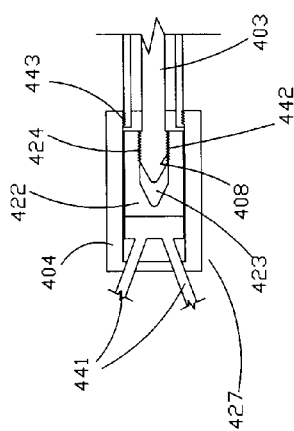

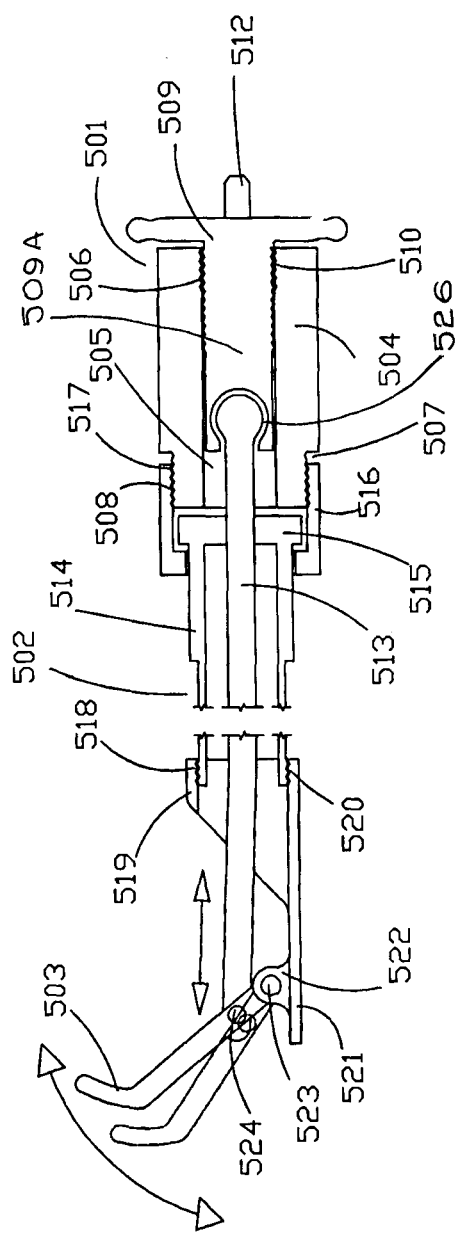
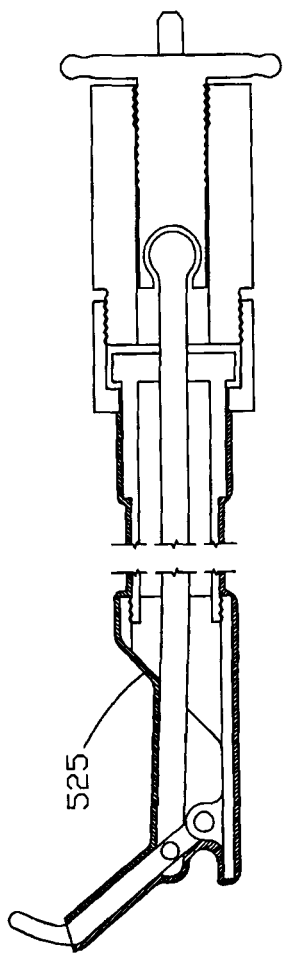
Figure 5 A
Figure 5 B

SURGICAL INSTRUMENT EQUIPMENT APPROPRIATE FOR MINI-INVASIVE SURGERY

CROSS REFERENCE TO RELATED APPLICATIONS

This application is a National Stage of International Application No. PCT/EC2010/000012 filed Jan. 6, 2010, claiming priority based on Argentinean Patent Application No. P 09 01 00135, filed Jan. 16, 2010, the contents of all of which are incorporated herein by reference in their entirety.

1) TITLE AND TECHNICAL FIELD OF THE INVENTION

The present invention relates to an equipment of surgical instruments suitable for minimally invasive surgery, defined by a number of operative pieces to be mounted inside the patient's cavity to be operated on.

2) STATE OF THE ART AND PROBLEMS TO SOLVE

At present, in the prior art, laparoscopic and endoscopic surgical instruments are known.

In laparoscopic surgeries, multiple access ports or channels are used with several incisions on the skin, one for each access device. In turn, each access port allows the entrance of one laparoscopic instrument at a time through only one operative channel. At present, since these laparoscopic instruments are rigid and function only on one directional axis, they are not adjustable to the different needs of variable angulation require either in space or at operative area.

In endoscopic surgery, instruments in use, contrary to laparoscopic instruments that have an extreme flexibility, do not have an own directional axis but instead the instrument is adapted to the artificial or natural duct along which it moves. In endoscopic surgery conducted through natural orifices, endoscopic clamp tips are of small size since they move inside operative ducts of the endoscopy and given their small operative area, they require a longer surgical time to attain the same result.

Either in laparoscopic as in endoscopic surgery, instruments presently used are already mounted and ready to be used before entering the working area.

The invention aims to solve the present limitations of laparoscopic and endoscopic surgical instruments, to reduce surgical times, to obtain more security while handling organs during surgery, to reduce the post operative pain, to get better aesthetic results and to circumscribe, by means of one or multiple access ways, different possibilities of video-assisted and minimally invasive diagnosis and surgical treatment. It also tends to solve those limitations found in the triangulation of monotrocar laparoscopic surgeries.

In the invention, this is attained by using:

Access device that enables simultaneous operation of several operative clamps through only one access and besides with said device, the access area to be used may be adjusted as needed.

Designs, devices, materials and media of minimum diameter and suitable to be intrasurgically mounted inside the patient's body such as the needle pliers which, it is worth mentioning, acquire three main advantages:

a) minimum access area or surface to be entered by means of a needle;

b) entrance of these needle pliers is direct without needing any additional access device; and c) good control and handling of organs or objects to be treated since the clamp head and tip are of larger diameter than that where the needle is introduced because the clamp head and tip are inserted by an access device, by a natural means or incision, and finally due to the function of the ensambling clamp, the mounting of the needle pliers is attained intrasurgically inside the patient's body, that is: two accesses are used so that the needle pliers be ready for use.

An articulated element of cauterization which allows spatial positioning and repositioning on different directional axis according to the angulation needed for the practice to be performed, improving performance at the surgical site.

3) OBJECT OF THE INVENTION

The object of the invention lies on the performance of surgical acts in which various operative devices inherent to surgery are manipulated through at least an access having an access device, said devices being mounted inside the patient's body, including an articulated element of cauterization and access of needle pliers through other accesses, allowing operation with several operative clamps that permit a clear maneuverability and control of the practice to be performed at different planes and angulations as the surgical technique may require, resulting in a minimum access surface and a greater operative scope. This is attained by:

Providing an access with an access device with a minimum incision and its opening may be adjusted according to the characteristics of the surgical act.

Providing an equipment of surgical instruments suitable for minimally invasive surgery that allows the interchange of operative tips according to the different stages of the surgery without needing to perform other access incisions.

Providing a needle plier having a puncture end that will not need any additional tools to perform the incision on the patient and that, in turn, said puncture end may permit an intrasurgical connection and to insert into the patient's body any kind of operative head to be used with no limitation as to diameters of said head.

Providing an equipment of surgical instruments suitable for minimally invasive surgery which clamp tips may rotate 360° whatever the configuration of the operative element may be.

Providing an equipment of surgical instruments suitable for minimally invasive surgery which access port can allow the entrance of operative tools which operative head is of greater diameter than the average transmission diameter of said tools, which can allow to combine the concept of minimal access with a surgical practice being safer than that of the laparoscopy due to the size of the operative ends of the tools.

Providing a mounting clamp that transports heads of the needle pliers to the interior of the patient's cavity in different surgical acts and that allows the intrasurgical mounting of the needle plier permitting its coupling inside the patient's body.

Providing an articulated element of cauterization that may adopt different angulations at the surgical site, overcoming the limitations of rigid working elements.

4) DESCRIPTION OF FIGURES

The present invention will be better understood by means of the figures, in which.

FIG. 3 A shows a view with the different shapes that the operative mounting device may adopt.

FIG. 3 B shows a perspective view of the front of the operative clamp.

FIG. 4 A shows a general lateral view of the needle pliers.

FIG. 4 B shows a detailed lateral view of the needle pliers connected to a double articulation head.

FIG. 4 C shows an upper view of the head of double articulation.

FIG. 4 D shows a detailed view of the head of single articulation.

FIG. 4 E shows a detailed lateral view of the head of elastic articulation.

FIG. 4 F shows a partial view according to plane A-A of FIG. 4 B.

FIG. 4 G shows a partial view according to plane B-B of FIG. 4 B.

FIG. 5 A shows a lateral detailed view of the cauterization device.

FIG. 5B shows a lateral detailed view of the cauterization device with the isolating coating.

5) DETAILED DESCRIPTION OF THE INVENTION

Figure 1:
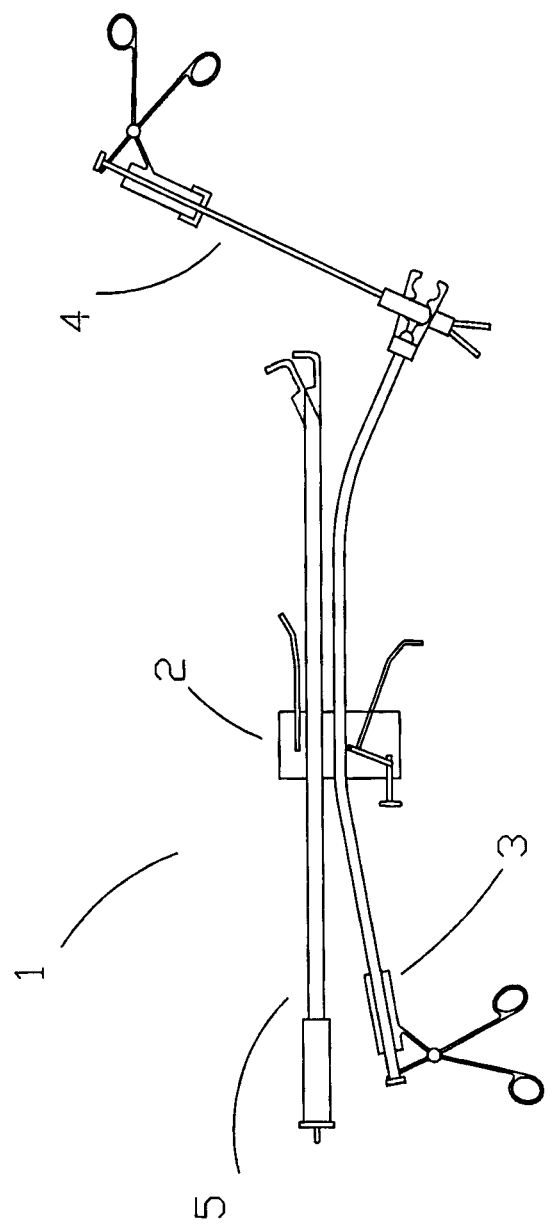
FIG. 1 shows the equipment of surgical instruments with all elements included: an access device, a device for surgical work, a mounting clamp and a cauterization device.

In FIG. 1 an equipment of surgical instruments (1) with all elements included is seen, comprised by an access device (2), an operative mounting device (3), a needle plier (4) and a cauterization device (5).

Figure 2:
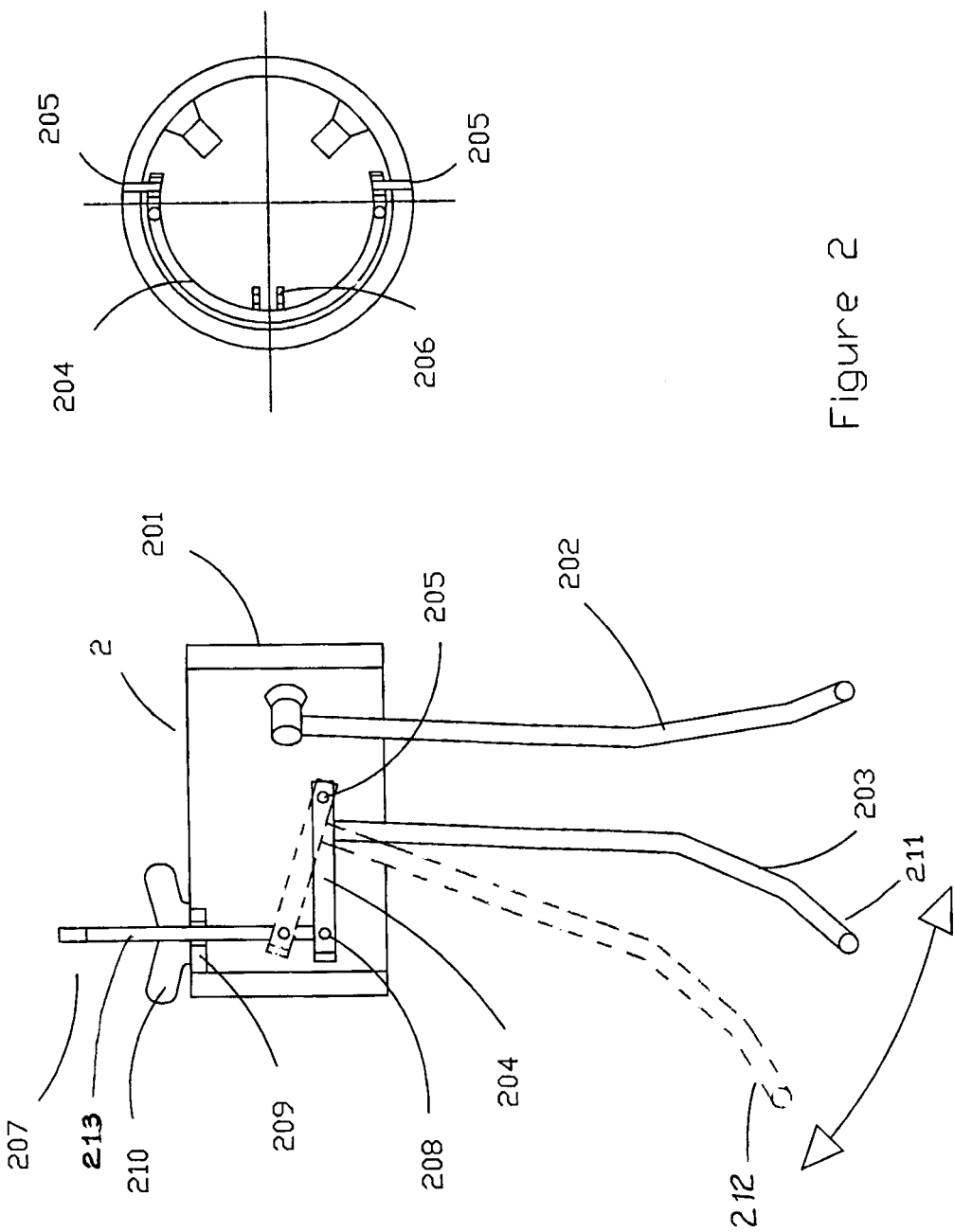
FIG. 2 shows a partial lateral view and a partial upper view of the access device.

FIG. 2 shows an access device according to the present invention that widely overcomes the prior art in the sense that facilitates its use and that fixes separators. The access device (2) consists of a rigid ring (201) from which at its inner side and opposite to each other, two extensions stem out in distal direction that act as separators, one extension will be the steady separator (202) tightly joined to the rigid ring and the other extension will be the movable separator (203), being movable with respect to the steady separator (202). Both separators are slightly bent towards the external side of the access device and all surfaces and angles are blunt. Distal ends show a "U" shape. The movable separator is tightly joined to a demilune (204) that pivots around bolts (205) with respect to the rigid ring. Therefore, the movable separator pivots with respect to the rigid ring.

Near the distal end of the rigid ring the demilune is lodged, which is joined to the rigid ring by bolts (205), at its ends, which allow its pivot. In the central part of the demilune, an articulation (206) is provided, which is connected to the opening adjusting device (207) by the corresponding bolt. Near the ends of the demilune, the movable separator is provided, tightly joined to said demilune.

On the internal face of the rigid ring of the access device, opposite to the steady separator and close to a proximal part of same, a lid (209) with a thru hole is provided. Inside the thru hole of the lid, the opening adjusting device (207) is provided. This is a threaded rod at its proximal part (213), and at its distal part it has flat sides opposing a central thru hole at its end which is connected to the articulation (206) by means of the bolt (208). The throttle (210) rests in the proximal face of the lid (209) in coincidence with the threaded portion (213) of the threaded rod.

When a rotation is given to the throttle, this, when rotating, causes a displacement of the threaded rod toward proximal part of the opening adjusting device (207), which drags, through the bolt (208) and the articulation (206) the demilune causing its pivot around the bolts (205). Therefore, a rotation around said bolts (205) of the movable separator occurs. In FIG. 2, in full lines, the movable separator in a first position (211) is seen and in dotted lines the same movable separator in a second opening position (212) is seen.

In FIG. 3A, a working mounting device is seen, which device is comprised by a control (301), a movement transmitting element (302) and an operative clamp (303) at different operative angulations. The movement transmitting element may be rigid or memorize the positioning and allows a 360° rotation of the operative clamp. The novelty of the present surgical element is the operative mounting clamp. This is designed not to work over the patient himself, with operations such as cut, cauterization, pressing, etc., but to tightly maintain the head of the needle plier. The movement of this operative plier is also known in the prior art: branches and articulations that transform a linear movement in a transverse one. The novel feature of this operative plier, and which is seen in FIG. 3B, is that it has at least a furrow (304) on each branch of its pliers, which allows to rigidly tighten the head of the needle pliers not permitting said head to rotate.

Figure 4A:
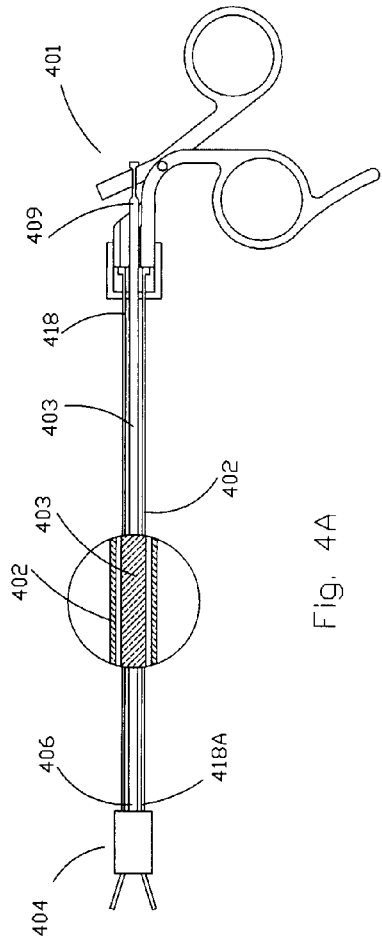
Figure 4B:
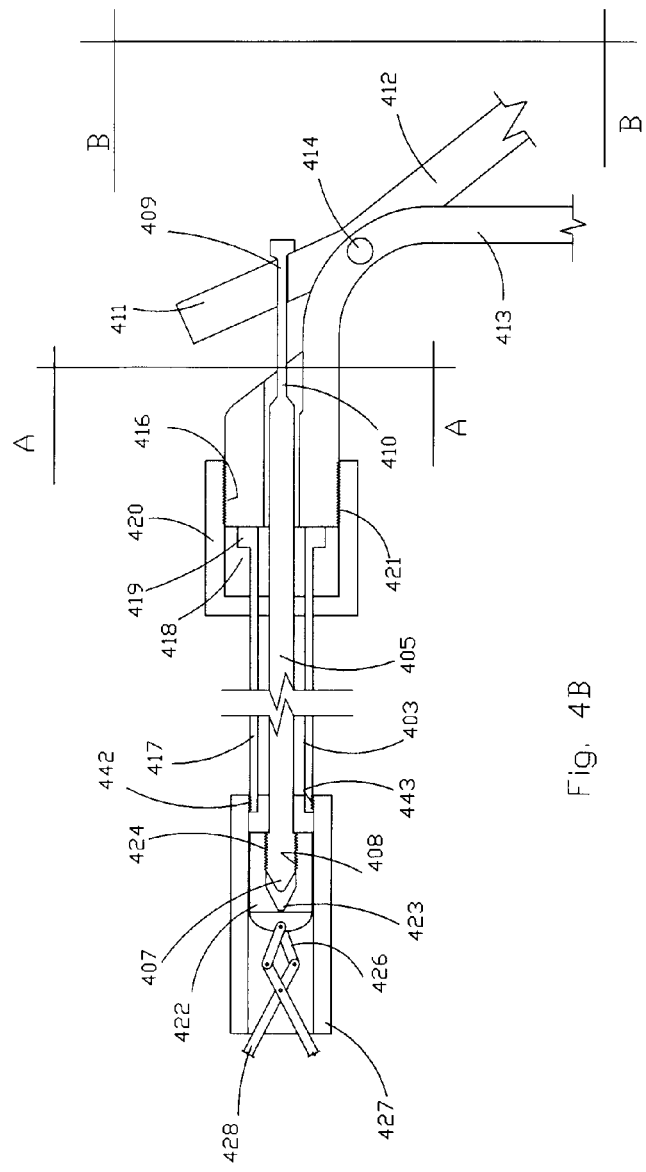

In FIG. 4A, a needle plier is seen comprised by a control (401), a sheath to connect to the head (head connecting sheath) (402) with its distal (418A) and proximal ends (418), with the connecting needle (403) provided inside, with its distal (406) and proximal (409) ends, and the operative head (404). In FIG. 4B, it is seen that the connecting needle (403) is comprised by a body (405), which is a rigid, thin, elongated and cylindric element, which distal end is sharp (407) and having an external needle plier thread (408) and, at its proximal end (409) it provides an insert made up by two opposite slots (410) near to said end. This portion of the connecting needle couples into the longitudinal slot (411) (see FIG. 4G) of the movable branch (412) of the control to attain the axial movement, which movement allows the connecting needle to function in combination with the operative head. The particular feature of the distal end, characterized for being sharp, allows the needle plier to be inserted through the patient's tissue to reach his inner body. Following the sharp end, an external connecting needle thread (408) is provided, which is threaded into the internal thread (424) of the driving intrahead device (422). The connecting needle (403) moves along the interior of the head connecting sheath (402).

The control of the needle plier has a movable branch (412) and a steady branch (413) joined at an articulation (414) (see FIG. 4 B). The movable branch has a slot into which the proximal end of the connecting needle is fitted. The steady branch has a furrow (415) with external thread (416) in its base, keeping open its upper part. This configuration allows that the connecting needle to fit either in the furrow of the steady branch as well as in the longitudinal slot (411) of the movable branch for assembling the equipment. The distal end of the control is flat, wherein the connecting sheath rests. The body (405) of the connecting needle passes freely by said furrow. In FIG. 4 F, a view by plane A-A of FIG. 4B is seen. In FIG. 4 G, a view by plane B-B of FIG. 4B is seen.

The head connecting sheath (402) has a body (417), which is a rigid, thin, elongated and tubular element (see FIG. 4 B). The proximal portion (418) finishes as a cylindric, washer type abut (419) and with a joint piece (420) with internal thread (421), which displaces over said abut and contacts the external thread (416) of the furrow of the steady branch of the control. This union does not allow the connecting sheath to move in longitudinal direction. The connecting sheath may be covered along all its extension by an isolating sheath. At its distal end, an external thread (442) is provided.

The operative head (404) comprises a body of working head (427), a driving intrahead device (422) and the driving elements of the clamp head (see FIG. 4 B).

The driving intrahead device (422) is a cylindric, solid device, which at its proximal part has an cavity (423) with internal thread (424) into which it couples to the thread (408) of the connecting needle (403). The driving intrahead device, at its distal part, is provided with driving elements of the clamp head, and is lodged inside the body of working head (427).

In a first embodiment, the driving element of the clamp tips is of double articulation, as seen in FIGS. 4B and 4C. The double articulation is made up by a pair of clamp tips (428) joined by bolts to a pair of clamp articulations (426). The clamp articulations are flat elements, with thru holes on each of their ends. A first bolt (425) joins the orifices of proximal ends of the clamp articulations to the driving intrahead device by means of its distal thru hole. The clamp tips have a first thru hole at their proximal ends and a second thru hole in the middle of said tips and the first hole. Both clamp tips are joined by means of second bolts (429) at their proximal ends to the distal ends of the clamp articulations. By means of a third bolt (430) at its second holes, they are joined to the body of working head (427). This set of elements make up an articulation which, when receiving the bi-directional movement of the driving intrahead device (422), causes the opening and closure of the clamp tips (428). The clamp tips show, at their distal ends, devices that allow pression, cut, disection, clipping, cauterization, suture, separators, etc. which belong to the prior art.

In a second embodiment, the driving element of the clamp tips is a single articulation, as seen in FIG. 4D. The body of working head (427) has a complete circumference (434) at its proximal end, the rest being only the basis (435). In the middle of the basis, a pair of flanges (436) opposite to a thru hole are provided. Between said pair of flanges, the proximal end of the single articulation (437) is lodged, which has a first thru hole, and this single articulation is joined by a bolt (438) to the pair of flanges (436). Near this first thru hole, a second thru hole is provided to which the distal end of the driving intrahead device is joined, by means of a bolt (439), and through a joining element (440). In this embodiment, a joining element (440) is provided between said driving intrahead device (422) and the single articulation (437). This joining element is joined to the driving intrahead device and, at its distal end, a thru hole is provided, where the bolt is coupled (439), which bolt drives the single articulation (437). By means of the control (401) of the needle plier, an axial movement of the driving intrahead device is attained which is transformed into an opening and closing movement of the single articulation (437).

In a third embodiment, the driving element of the clamp tips is an elastic type articulation, as seen in FIG. 4E. The body of working head (427) has, at its proximal end, an internal thread (443) that finishes, at its distal end, in tubular shape. By the interior of the head, the driving intrahead device (422) moves freely, having, at the proximal side, an orifice (423) with internal thread (424) where the extenal thread (408) of the connecting needle (403) is coupled. Following the internal thread and in distal direction of the bolt, the latter is divided into two elastic, "V" shaped branches (441), forming the clamp tips. Each of these "V" shaped branches finishes in the form of a clamp to perform pression, dissection, cutting, clipping, separating, suturing, cauterizing, etc. When the driving chuck is displaced in bi-directional movement (from proximal to distal or vice versa), given the elastic feature of the "V" shaped branches, the latter are driven apart or put together causing the opening or closing of the clamp tips (441).

In FIG. 5, a cauterization device is seen, comprising a control (501), a movement transmitting set (502) and articulation tool of the cautery (503).

The movement transmitting set comprises a driving chuck (513) and the head connecting sheath.

The control comprises a handle (504), being cylindric and isolating, with an axial thru hole (505) that has an internal thread (506). At its distal end it has, on the outer side, a cut (507) with an external thread (508) Inside the handle, a cautery driving device, comprising a cylindric piece (509A) with an external thread (510) in the distal end and an isolated turning wrench (509) in its proximal end is provided. At this end, an electricity connector (512) is also provided for the cautery. The distal end of the cylindric piece (509A) has a cylindrical cavity (526) in the shape of a furrow configured to receive an end of the driving chuck (513), so that the former may rotate around the latter and allow its pushing or retraction together with the movement of the cautery driving device. An electric continuity is provided between the electricity connector and the distal end that receives the end of the driving chuck.

The head connecting sheath has a body (514), which is a rigid, thin, elongated and tubular element. Inside this head connecting sheath, the driving chuck is lodged. The proximal portion finishes in a cylindric, washer type abut (515) and with a joint piece (516) with internal thread (517), which displaces over said abut, and contacts the external thread (508) of the cut (507) of the control. This union does not allow the connecting sheath to move in longitudinal direction. The connecting sheath may be covered along all its extension by an isolating sheath. At its distal end, an external thread (518) is provided.

The articulation tool of the cautery comprises a head, the articulation and the cautery itself.

The head (519) is a piece with its proximal end being cylindric, with an internal thread (520) where the external thread (518) of the head connecting sheath is threaded. Near its distal end, which shows only a basis (521), a pair of flanges (522) is provided on which the cautery (503) pivots by a first bolt (523). The cautery has an orifice for the second bolt (524) that is joined to the distal end of the driving chuck. The rotation of the cautery driving device causes an axial displacement of the driving chuck and, due to the lever in the head end, transforms this linear movement into an angular movement of the cautery.

In FIG. 5B, the cautery with an insulated coating (525) is observed; said coating covers the cautery except for the distal end of the cautery itself.

Having described and defined the nature of the invention as well as the manner in which same can be put into practice based on its main object, the following is claimed as invention and of exclusive ownership:

1. An equipment of surgical instruments suitable for minimally invasive surgery, wherein the equipment of surgical instruments comprises:
    an access device with two separators configured to access a patient's body, and components configured to be simultaneously inserted inside said patient's body via the access device, the components including an operative mounting device comprised by a handle, a movement transmitting element and an operative mounting clamp configured to hold a needle plier;

the needle plier comprised by a control, a head connecting sheath including distal and proximal ends, a connecting needle including distal and proximal ends provided within the head connecting sheath, and an operative head; and a cauterization device comprising a control, a movement transmitting set and a cautery, wherein the access device comprises the two separators and a rigid ring, the two separators extending from an inner side of the rigid ring and located opposite to each other, the two separators stem out in distal direction, and include a steady separator tightly joined to the rigid ring and a movable separator being movable with respect to the steady separator.

2. The equipment of surgical instruments suitable for minimally invasive surgery according to claim 1, wherein the movable separator is tightly joined to a demilune that pivots around bolts with respect to the rigid ring.

3. The equipment of surgical instruments suitable for minimally invasive surgery according to claim 2, wherein at an inner face of the rigid ring, opposite to the steady separator and next to a proximal portion of a lid, the lid is provided with a thru hole inside which an adjustable opening device is provided with its proximal end being threaded, driven by a throttle which abuts a proximal face of said lid and whose distal end is connected to an articulation of the demilune by means of a bolt.

4. The equipment of surgical instruments suitable for minimally invasive surgery according to claim 1, wherein the movement transmitting element of the operative mounting device is configured to return to a positioning when displaced therefrom and the operative mounting clamp is configured to perform a 360° rotation.

5. The equipment of surgical instruments suitable for minimally invasive surgery according to claim 4, wherein the operative mounting clamp has two branches with at least one furrow on each branch, as an engagement means to the head of the needle plier.

6. An equipment of surgical instruments suitable for minimally invasive surgery, wherein the equipment of surgical instruments comprises:

an access device with two separators configured to access a patient's body, and components configured to be simultaneously inserted inside said patient's body via the access device, the components including an operative mounting device comprised by a handle, a movement transmitting element and an operative mounting clamp configured to hold a needle plier;

the needle plier comprised by a control, a head connecting sheath including distal and proximal ends, a connecting needle including distal and proximal ends provided within the head connecting sheath, and an operative head; and a cauterization device comprising a control, a movement transmitting set and a cautery, wherein the connecting needle comprises a cylindric, rigid, thin and elongated body, and the needle's distal end is sharp with an external needle plier thread and the needle's proximal end inserts into a slot of a movable branch of the control.

7. The equipment of surgical instruments suitable for minimally invasive surgery according to claim 6, wherein a driving intrahead device is cylindric, the proximal side of the driving intrahead device has a cavity with internal threads, the distal side of the driving intrahead device is provided with driving media of clamp tips, and the driving intrahead device is lodged inside a body of working head along which the driving intrahead device moves axially and where the internal thread couples to the external thread of the connecting needle.

8. The equipment of surgical instruments suitable for minimally invasive surgery according to claim 7, wherein a driving element of the clamp tips is of double articulation, comprised by a pair of clamp tips joined by their proximal ends by means of bolts to the distal ends of a pair of clamp flat articulations which, in turn, are joined by their proximal ends by means of a bolt to the distal end of the driving intrahead device; and the pair of clamp tips having a second orifice between the middle of the tips and the proximal end, being joined by a bolt at said second holes, to the body of the working head.

9. The equipment of surgical instruments suitable for minimally invasive surgery according to claim 7, wherein the driving element of the clamp tips is a single articulation and the body of working head has a complete circumference at its proximal end, the rest being only the basis, in the middle of the basis, a pair of flanges is provided opposing a thru hole; between said pair of flanges, the proximal end of a single articulation is found, which articulation has a first thru hole and this single articulation is joined by a bolt to the pair of flanges; near this first thru hole, a second thru hole is provided, which is joined, by means of a bolt and through a joining element, to the distal end of the driving intrahead device.

10. Equipment of surgical instruments suitable for minimally invasive surgery according to claim 7, wherein a driving element of the clamp tips is an elastic type articulation, where the body of working head has at its distal end a pair of elastic, "V" shaped branches, forming the clamp tips.

11. The equipment of surgical instruments suitable for minimally invasive surgery according to claim 6, wherein the control comprises a movable branch and a steady branch joined at an articulation, and said movable branch has a slot in which a proximal end of the connecting needle fits, and the steady branch has a furrow with external thread in its base, keeping the upper part open in which the connecting needle fits.

12. The equipment of surgical instruments suitable for minimally invasive surgery according to claim 6, wherein the head connecting sheath is a tubular, rigid, thin and elongated element, and whose proximal portion finishes with a cylindric, washer type abut and with a fixing thread with internal thread, and the distal end shows an external thread where the external thread is threaded to the internal thread at the proximal side of a needle plier head, and where the fixing thread (420) moves over the washer type abut, and contacts the external thread (416) of a furrow of the steady branch of the control (401).

13. The equipment of surgical instruments suitable for minimally invasive surgery according to claim 6, wherein the head connecting sheath is provided along its entire extension with an electric isolation.

14. An equipment of surgical instruments suitable for minimally invasive surgery, wherein the equipment of surgical instruments comprises:

an access device with two separators configured to access a patient's body, and components configured to be simultaneously inserted inside said patient's body via the access device, the components including an operative mounting device comprised by a handle, a movement transmitting element and an operative mounting clamp configured to hold a needle plier;

the needle plier comprised by a control, a head connecting sheath including distal and proximal ends, a connecting needle including distal and proximal ends provided within the head connecting sheath, and an operative head; and a cauterization device comprising a control, a movement transmitting set and a cautery, wherein the control comprises a cylindric and isolating handle, with an axial thru hole comprising an internal thread and the distal end of the handle has, on the outer side, a cut with an external thread;

a cautery driving device, comprising a cylindric piece with an external thread in the distal end and an isolating turning wrench in its proximal end are provided inside the handle, a distal end of the cylindric piece includes a cylindrical cavity in the shape of a furrow of a proximal end of a driving chuck such that rotation of the cylindric piece around the driving chuck allows the axial displacement of the driving chuck; and at the proximal end of the turning wrench, an electricity connector is also provided for the cautery.

15. The equipment of surgical instruments suitable for minimally invasive surgery according to claim 14, wherein the head connecting sheath, also isolated, has an external thread (518) at its distal end, which is threaded to a head by the internal thread at its proximal end.

16. The equipment of surgical instruments suitable for minimally invasive surgery according to claim 15, wherein at the distal end of the head, a basis is found wholly integrated to a pair of flanges on which the articulation tool of the cautery pivots by means of a first bolt driven through a second bolt which is joined to the distal end of the driving chuck.

17. The equipment of surgical instruments suitable for minimally invasive surgery according to claim 16, wherein the cautery has, along its entire extension except at its distal end, an electric insulation.

* * * * *